(12) United States Patent
Gandyra et al.

(10) Patent No.: US 9,671,220 B2
(45) Date of Patent: Jun. 6, 2017

(54) DEVICE FOR DETERMINING THE 3D COORDINATES OF AN OBJECT, IN PARTICULAR OF A TOOTH

(75) Inventors: Michael Gandyra, Rosenheim (DE); Marcus Steinbichler, Neubeuern (DE)

(73) Assignee: STEINBICHLER OPTOTECHNIK GMBH, Neubeuern (DE)

( * ) Notice: Subject to any disclaimer, the term of this patent is extended or adjusted under 35 U.S.C. 154(b) by 1845 days.

(21) Appl. No.: 12/560,704

(22) Filed: Sep. 16, 2009

(65) Prior Publication Data

US 2010/0239136 A1 Sep. 23, 2010

(30) Foreign Application Priority Data

Sep. 18, 2008 (DE) .................. 10 2008 047 816

(51) Int. Cl.
| | |
|---|---|
| G06K 9/00 | (2006.01) |
| G01B 11/245 | (2006.01) |
| G01B 11/03 | (2006.01) |
| G01B 11/25 | (2006.01) |
| G01C 11/02 | (2006.01) |
| A61C 9/00 | (2006.01) |

(52) U.S. Cl.
CPC ............ G01B 11/245 (2013.01); A61C 9/006 (2013.01); G01B 11/03 (2013.01); G01B 11/2513 (2013.01); G01C 11/02 (2013.01); *A61C 9/0053* (2013.01)

(58) Field of Classification Search
USPC ............. 600/407, 425; 356/603, 604, 606; 382/154
See application file for complete search history.

(56) References Cited

U.S. PATENT DOCUMENTS

| | | | | |
|---|---|---|---|---|
| 5,339,154 A | * | 8/1994 | Gassler et al. | 356/604 |
| 5,347,454 A | * | 9/1994 | Mushabac | G05B 19/4207 433/214 |
| 5,372,502 A | * | 12/1994 | Massen et al. | 433/215 |
| 5,712,803 A | | 1/1998 | Garuet-Lempirou | |
| 5,969,822 A | | 10/1999 | Fright et al. | |
| 7,335,876 B2 | * | 2/2008 | Eiff et al. | 250/234 |
| 2002/0171847 A1 | * | 11/2002 | Fukumoto et al. | 356/606 |
| 2003/0164952 A1 | * | 9/2003 | Deichmann et al. | 356/603 |
| 2004/0252312 A1 | * | 12/2004 | Chen | A61C 9/006 356/603 |
| 2005/0089214 A1 | * | 4/2005 | Rubbert et al. | 382/154 |
| 2005/0142517 A1 | * | 6/2005 | Frysh et al. | 433/173 |
| 2005/0202363 A1 | * | 9/2005 | Osterwalder | A61C 9/0006 433/29 |
| 2006/0094951 A1 | * | 5/2006 | Dean et al. | 600/407 |

(Continued)

FOREIGN PATENT DOCUMENTS

| | | |
|---|---|---|
| DE | 3810455 | 10/1989 |
| DE | 4206836 | 9/1993 |

(Continued)

*Primary Examiner* — Sean K Hunter
*Assistant Examiner* — Gregory Lultschik
(74) *Attorney, Agent, or Firm* — Dilworth & Barrese, LLP.

(57) ABSTRACT

A scanner is used for scanning an object, in particular one or more teeth (13, 14, 15) or a dental cast. An improved scanner comprises a carrier (2) on which a plurality of projectors (4) for projecting a pattern onto the object and a plurality of cameras (5) for recording the object are provided one beside the other in an array.

15 Claims, 4 Drawing Sheets

(56) References Cited

U.S. PATENT DOCUMENTS

| | | | |
|---|---|---|---|
| 2006/0269896 A1* | 11/2006 | Liu et al. | 433/29 |
| 2007/0188601 A1* | 8/2007 | Rohaly | H04N 13/0217 348/47 |
| 2007/0223009 A1 | 9/2007 | Erfling et al. | |
| 2007/0299338 A1* | 12/2007 | Stevick et al. | 600/425 |
| 2008/0060854 A1* | 3/2008 | Perlin | G06F 3/0425 178/18.03 |
| 2008/0101688 A1* | 5/2008 | Quadling et al. | 382/154 |
| 2008/0118143 A1* | 5/2008 | Gordon et al. | 382/154 |
| 2009/0231649 A1* | 9/2009 | Sirat | 359/9 |

FOREIGN PATENT DOCUMENTS

| | | |
|---|---|---|
| DE | 19581099 | 9/1997 |
| DE | 19634797 | 3/1998 |
| DE | 102004052199 | 4/2006 |
| DE | 102006013584 | 9/2007 |
| JP | 61-162706 | 7/1986 |

\* cited by examiner

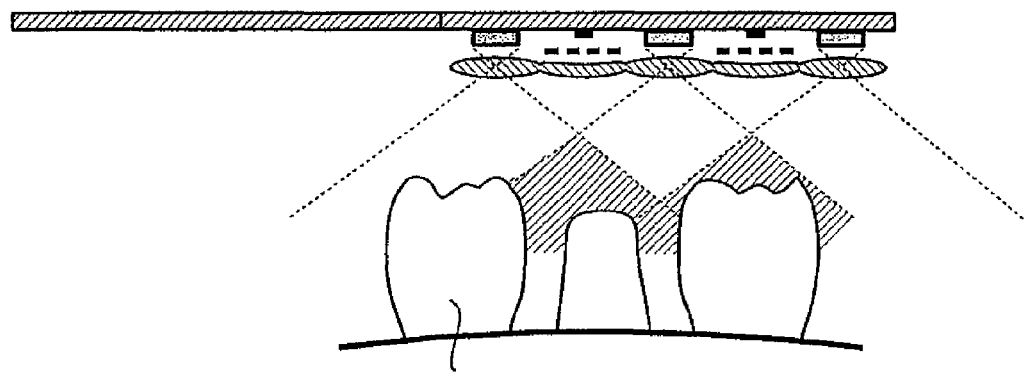
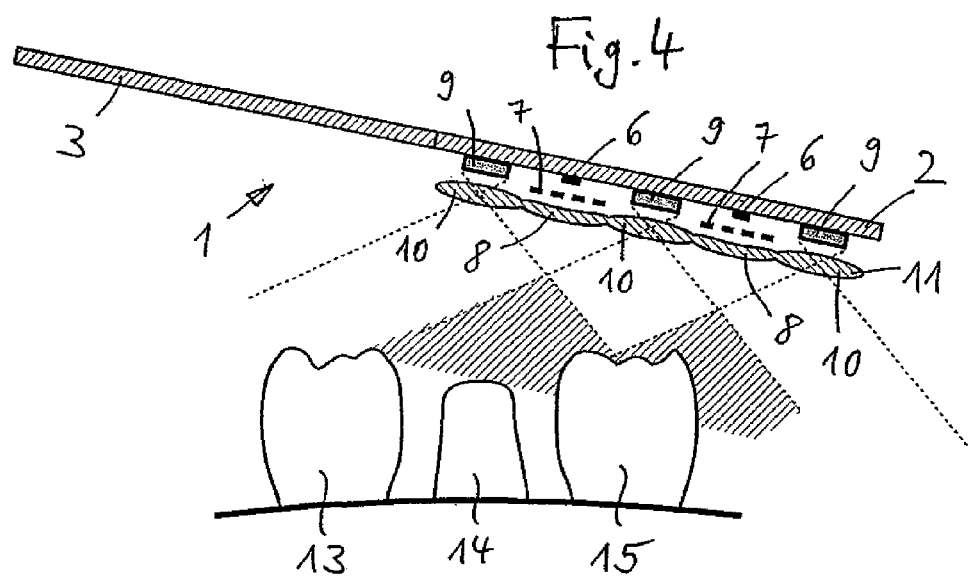
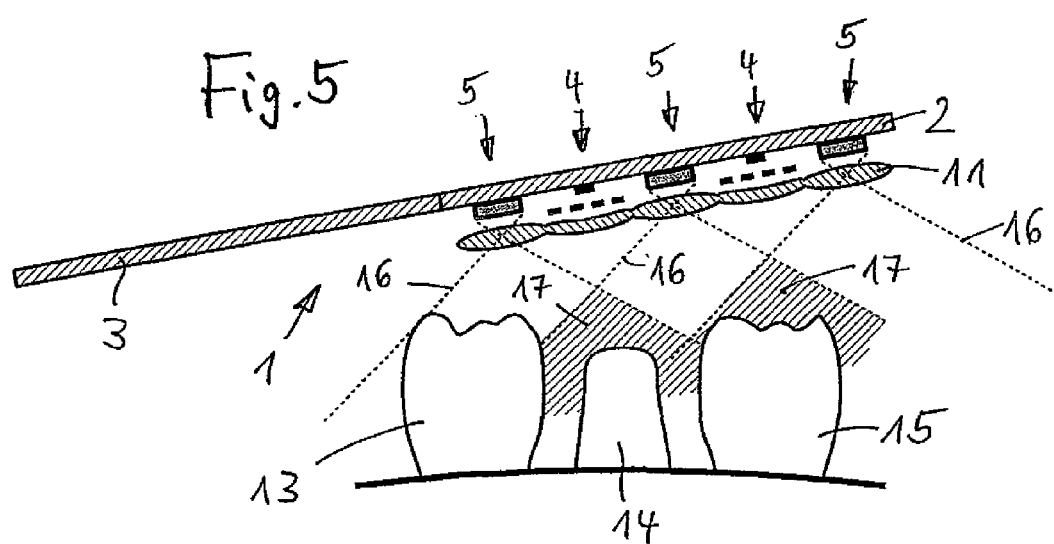

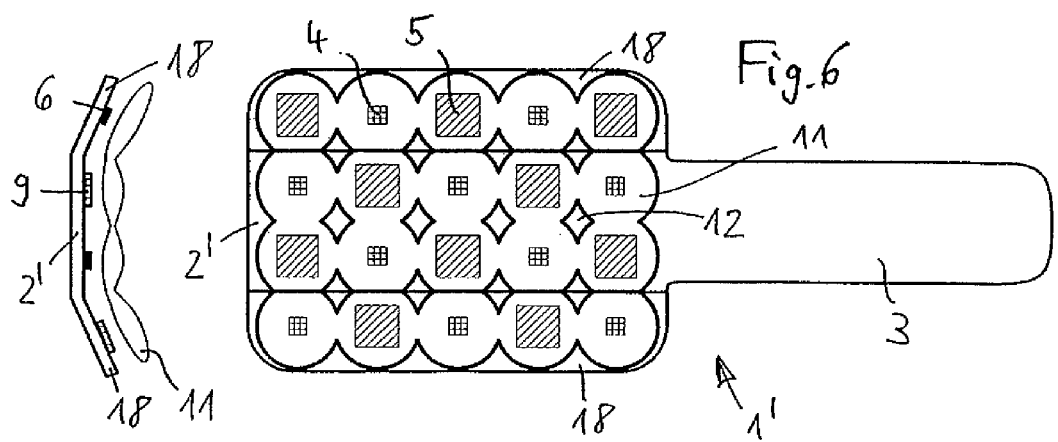
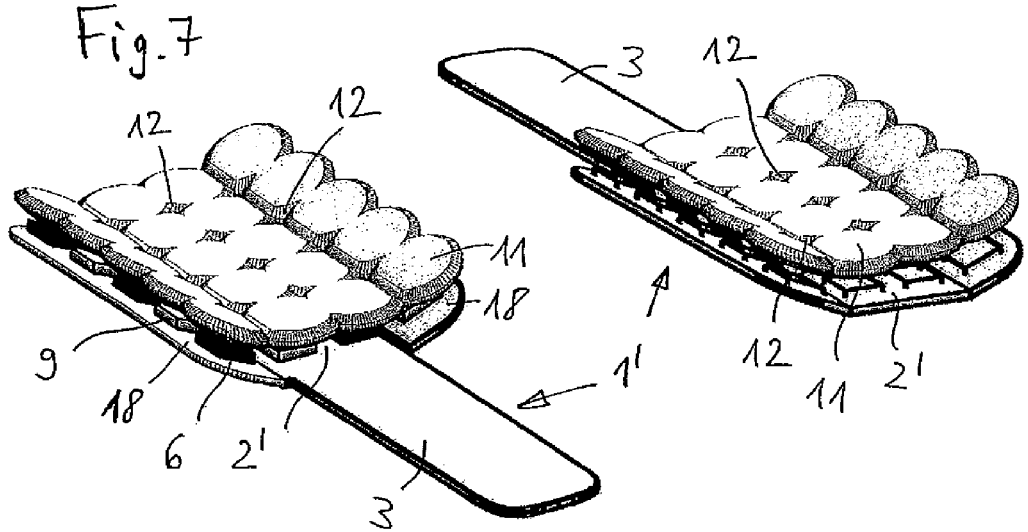
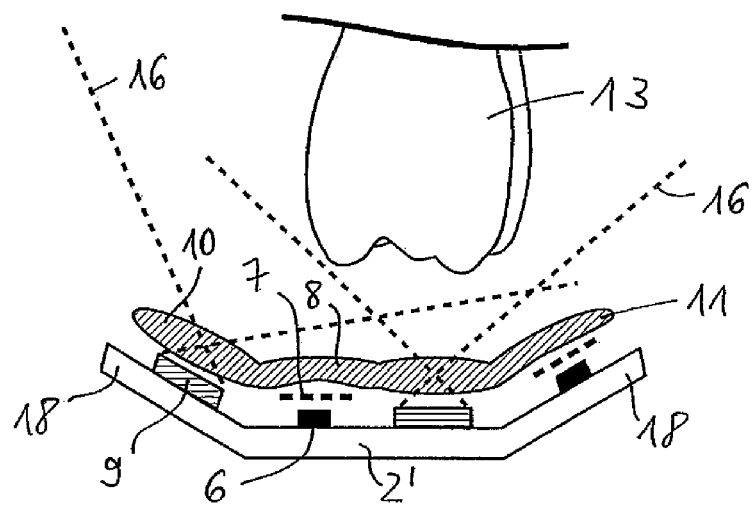

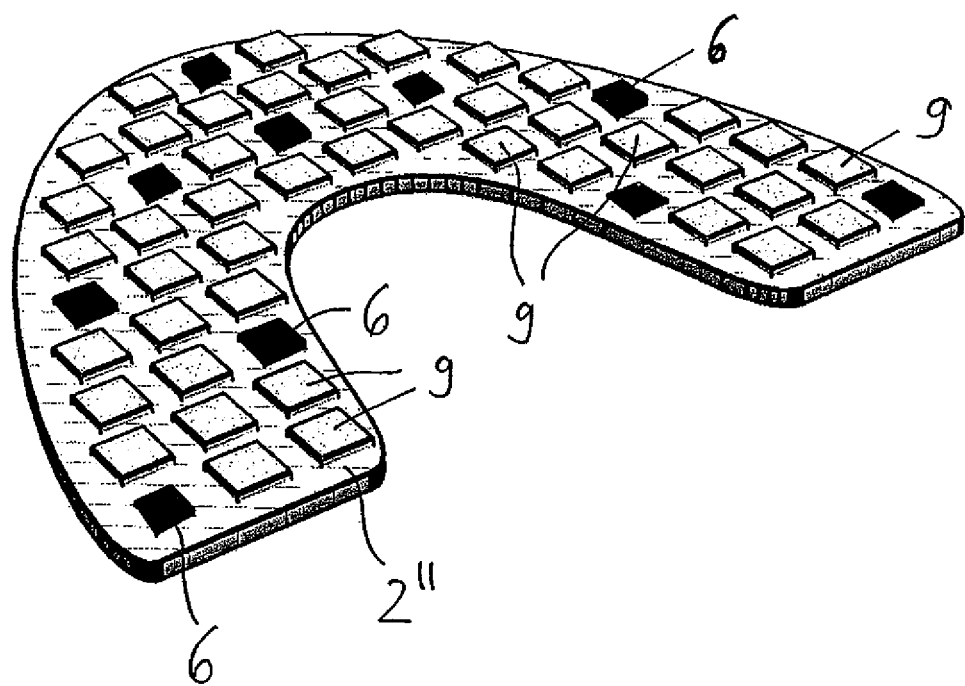

DEVICE FOR DETERMINING THE 3D COORDINATES OF AN OBJECT, IN PARTICULAR OF A TOOTH

BACKGROUND OF THE INVENTION

This invention relates to a scanner for scanning an object, in particular one or more teeth or a dental cast, and a device for determining the 3D coordinates of an object, in particular of one or more teeth or a dental cast. Teeth in the sense of the invention are understood to be prepared teeth and also dental prostheses.

Devices and methods for determining the 3D coordinates of an object are already known. EP 299 490 B2 describes a method for producing a dental prosthesis, in which isoheight or contour lines are generated on the ground-down tooth and its surroundings, the lines are detected with an optoelectronic means, in particular a video camera, the values detected are entered in a computer, and the spatial structure of the tooth and the dental prosthesis is calculated. With reference to the structure thus calculated, the dental prosthesis can be fabricated.

From the non-prepublished German Patent Application 10 2007 060 263.6 with the older priority, there is known a device for determining the 3D coordinates of an object, in particular of one or more teeth or a dental cast, by means of a scanner for scanning an object and an evaluation means for determining the 3D coordinates of the object from the images recorded by the scanner. The scanner comprises a projector for projecting a pattern onto the object and a camera, which comprises a recording optics with a first image optics and a second image optics and an image sensor.

SUMMARY OF THE INVENTION

It is the object of the invention to propose an improved scanner and an improved device as mentioned above.

In accordance with the invention, this object is solved by a scanner with the features herein. The scanner is used for scanning an object, in particular one or more teeth, wherein one or more or all teeth can be prepared. The term of preparing on the one hand comprises the dental preparation, i.e. for instance grinding down a tooth stump, and on the other hand the preparation advantageous or necessary for scanning a tooth with an optical measurement technique, for instance spraying the region to be scanned with white spray.

The scanner comprises a carrier on which a plurality of projectors for projecting a pattern onto the object and a plurality of cameras for recording the object are provided in an array. The projectors can be arranged as an array. The arrangement of the projectors and carriers in accordance with the invention is suitable in particular for use under cramped space conditions and in hard-to-reach areas, as they exist for instance in the oral cavity of a patient, in which the teeth should be scanned. The multitude of cameras ensures that a sufficient number of different images can be made for evaluation. The multitude of projectors ensures that a sufficient number of patterns can be projected onto the regions of the teeth to be scanned.

The scanner of the invention in particular can be formed as a miniaturized scanner. It is particularly useful for scanning teeth in the mouth of a patient. However, it is also particularly useful for other applications in which the objects to be scanned are hard to reach. In particular, the scanner of the invention can be useful for an endoscopic digitization and/or in hard-to-reach cavities and/or channels of machines and/or apparatuses.

Each image sensor generates a 2D image. From the 2D images, the 3D coordinates of the object can be determined. This can be accomplished by a measurement method, which is based on the evaluation of a plurality of 2D images on which the same object points are imaged. In this method, the same features can be found and correlated by using suitable algorithms in different 2D images. In a calibrated system, i.e. when the location and orientation of the cameras are known, a distance value and hence a 3D coordinate—within the coordinate system of the scanner—can be calculated for each object point located in different 2D images. To find the same features of the object in the different 2D images, patterns are projected onto the object. By means of the projected pattern(s), the object points corresponding to each other can be found in different 2D images. In this way, a 3D point cloud can be determined from the 2D images, which represents the surface of the object.

Furthermore, it is possible to combine several 3D point clouds to one complete 3D point cloud, which represents the entire object. For this purpose, a plurality of 3D point clouds can each be determined from different directions. The scanner can be moved around the object, in order to cover several or all regions of the object.

Advantageous developments are described herein.

Advantageously, the projectors and cameras are provided in a two-dimensional arrangement on the carrier.

The projectors and cameras can alternately be arranged on the carrier. It is possible to arrange a camera beside a projector and then repeat this, so that the projectors and cameras are alternatingly arranged in a ratio of 1:1. This pattern can correspondingly be expanded in area. It is, however, also possible to provide more projectors than cameras or more cameras than projectors. The arrangement can be regular or irregular.

The projectors each can comprise a light source, a mask and a projector optics. The light source preferably is an LED. The projector optics can consist of one or more lenses. The mask can be formed by an LCD.

Advantageously, the mask and the projector optics, in particular a lens of the projector optics, form a composite unit. Particularly advantageously, the mask is vapor-deposited onto the projector optics, in particular onto a lens of the projector optics. The mask in particular is manufactured as a vapor-deposited chromium mask.

In accordance with another advantageous development, the projectors each comprise a pattern projector and a projector optics. The pattern projector can be a DLP or LCOS.

The cameras each can comprise an image sensor, in particular a CCD sensor or a CMOS sensor, and a camera optics. The camera optics can comprise one or more lenses.

It is possible that each projector and/or each camera each includes one projector optics and/or one camera optics. In certain cases, however, it may be advantageous to combine several or all projector optics and/or several or all camera optics to one system optics. The system optics can be formed in one piece. It can be manufactured as a combination of several or all optics or lenses.

The carrier on which the projectors and cameras are provided can have a flat shape. In certain applications, however, it is advantageous when the carrier has angled regions. In particular, the carrier can have angled sides. The carrier preferably is concave.

In accordance with another advantageous development, the carrier has the shape of a dental arc.

In a device for determining the 3D coordinates of an object, in particular of a tooth, the object underlying the invention is solved by the features of claim 10. The device comprises a scanner in accordance with the invention for scanning the object or tooth and an evaluation means, in particular a computer, especially a PC including the associated software, for determining the 3D coordinates of the object from the images recorded by the scanner.

For performing the invention, a tracking system is not required. In certain cases, however, it may be advantageous when the device of the invention comprises a tracking system for determining the location and orientation of the scanner. The tracking system can be formed in that the scanner includes one or more sensors for detecting the location and orientation of the scanner. In particular, the tracking system can be formed in that the scanner includes acceleration sensors and/or gyrometers. It is possible that the information of the sensor(s) for detecting the location and orientation of the scanner and/or the acceleration sensor(s) and/or the gyrometer(s), in particular their 6D information, is calculated back by time integration on the location and rotary position of the scanner. Instead or in addition, however, another tracking system can also be used, in particular an infrared tracking system.

BACKGROUND OF THE INVENTION

Embodiments of the invention will be explained in detail below with reference to the attached drawing, in which:

FIG. 4 shows the scanner of FIG. 3 in a position inclined to the right,

FIG. 5 shows the scanner of FIG. 3 in a position inclined to the left,

FIG. 6 shows a modification of the scanner of FIGS. 1 to 5, whose carrier has angled sides, FIG. 7 shows the scanner of FIG. 6 in two perspective representations, FIG. 8 shows a section through the scanner of FIGS. 6 and 7, and FIG. 9 shows another modified scanner, whose carrier has the shape of a dental arc.

DESCRIPTION OF THE PREFERRED EMBODIMENTS

Figure 1:
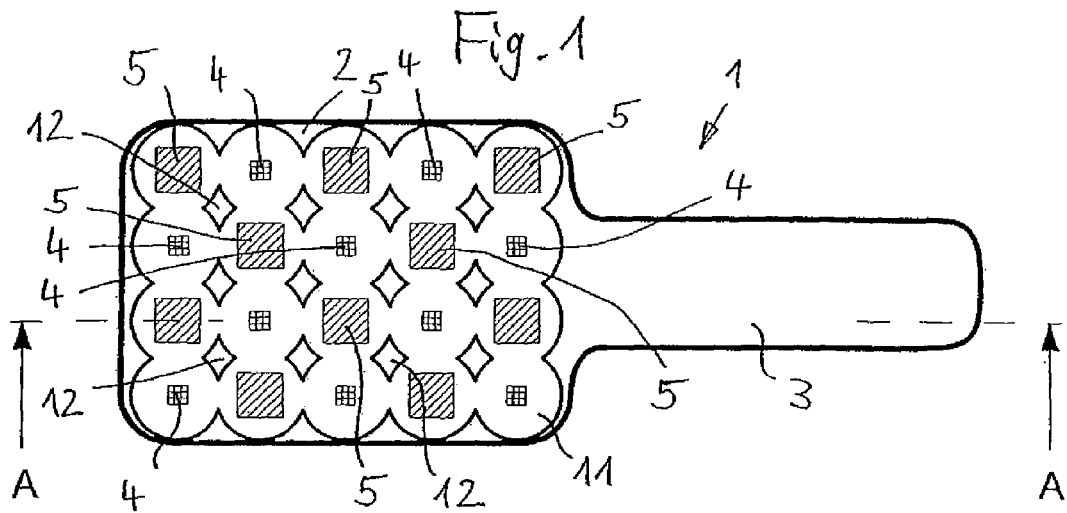
FIG. 1 shows a scanner in a view from above.

FIGS. 1 to 5 show a scanner 1 which comprises a flat carrier 2 and a handle part 3. On the carrier 2, ten projectors 4 and ten cameras 5 are provided one beside the other in a two-dimensional arrangement ("array"). The projectors 5 and the cameras 5 are alternately arranged on the carrier 2. In the uppermost row, from the left to the right, a camera 5, a projector 4, a camera 5, a projector 4 and a camera 5 are disposed. In the second row, from the left to the right, a projector 4, a camera 5, a projector 4, a camera 5 and a projector 4 are disposed. The third and fourth rows are configured like the first and second rows. In both directions, the projectors 4 and the cameras 5 alternate in a ratio of 1:1.

Figure 2:
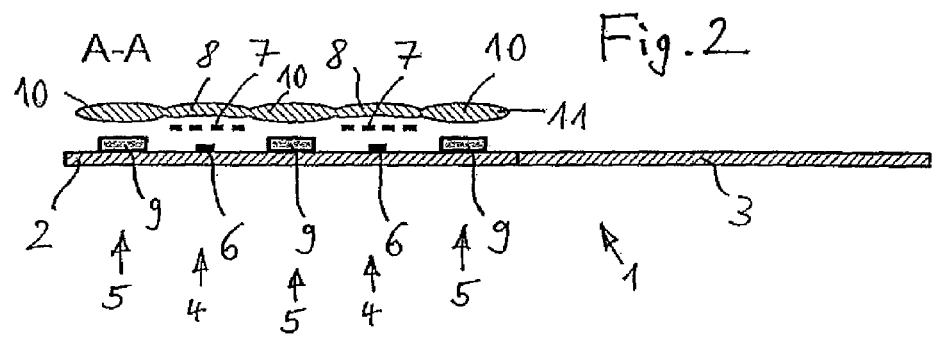
FIG. 2 shows a section along line A-A in FIG. 1.

FIG. 2 shows that each projector 4 comprises a light source 6, a mask 7 and a projector optics 8. The light source 6 is formed by an LED. The mask 7 is formed by a slide or LCD. The projector optics 8 consists of a lens.

Each camera 5 comprises an image sensor 9 and a camera optics 10. The image sensor 5 is a CCD image sensor or CMOS image sensor. The camera optics 10 consists of a lens.

In the embodiment of FIGS. 1 to 5 all projector optics 8 and all camera optics 10 are combined to one system optics 11. The system optics 11 is made in one piece. It each includes gaps 12 in the respective points of intersection of two adjacent projectors 4 and cameras 5.

Figure 3:
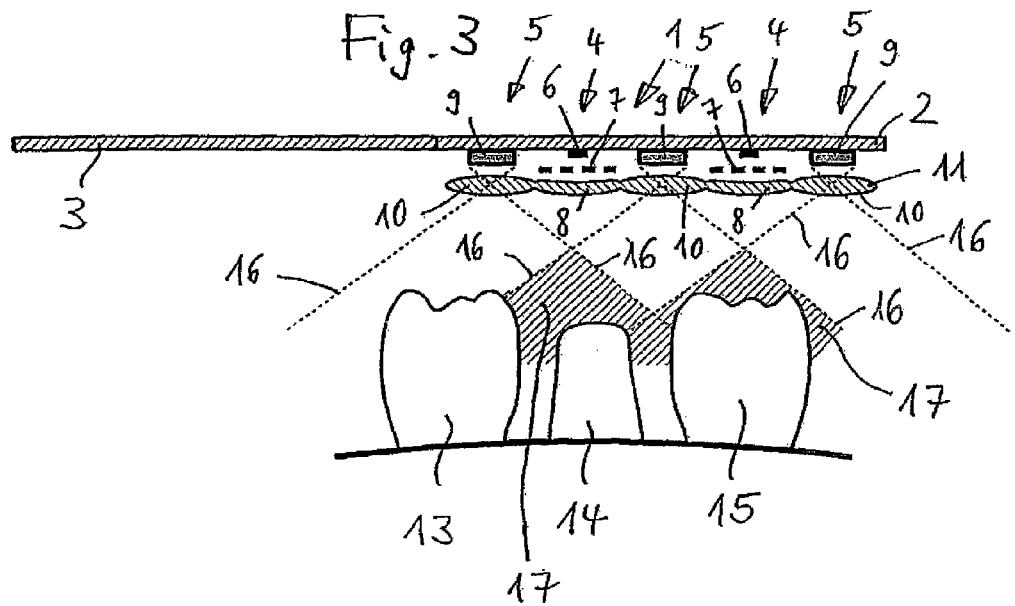
FIG. 3 shows the scanner of FIGS. 1 and 2 with a group of teeth.

In FIGS. 3 to 5, three teeth 13, 14, 15 are shown in addition to the scanner 1. The tooth 14 is ground down, the adjacent teeth 13, 15 are not ground down and form the surroundings of the ground-down tooth 14. Furthermore, the conical fields of view 16 of the image sensors 9 are illustrated in FIGS. 3 to 5. The regions 17, which are detected, i.e. "seen", by at least two image sensors 9 each, are shown hatched.

FIGS. 3 to 5 show a possible time sequence when scanning the teeth 13, 14, 15. Due to the fact that the scanner 1 is guided around the teeth 13, 14, 15, sufficient data can be obtained for the entire object representation.

In the modification of the scanner shown in FIGS. 6 to 8, components described already, which are provided with the same reference numerals, will not be explained again. Here, the carrier 2' of the scanner 1' has angled regions, i.e. angled sides 18. The carrier 2' has a concave shape. The angled sides 18 serve to record even more data of better quality on the tooth flanks.

FIG. 9 shows a further modification of a scanner with a carrier 2", which has the shape of a dental arc. The projectors 4 and the cameras 5 are arranged in the form of a dental arc.

The measurement method for determining the 3D coordinates of the objects or teeth can be based on a photogrammetric evaluation of a plurality of individual images, i.e. on the method of observing the object with a plurality of cameras and of finding and correlating the same features in the individual images by using suitable algorithms. A specific region of the object or tooth can be covered by an individual image. To cover the entire object or the entire tooth or several or all teeth and possibly also their surroundings, the individual images recorded by the cameras can be combined to one total image. This procedure is referred to as "registering" or "matching". The scanner can be moved around the object, in order to cover several or all regions of the object. In this way, a total object representation can be produced from a plurality of total images.

The pattern to be projected can be stochastic or ordered. It can consist of lines or cross gratings. It can be a time-constant or time-variable or sequential pattern. The pattern can be any graphical pattern (dots, lines, gratings etc.). The pattern can be a grey-scale pattern or a color pattern. The pattern can be projected with transmitted light, for instance as a chromium mask (slide) or as an LED projection. However, the pattern can also be projected by reflection, for instance as an LCOS or DLP projection.

The invention provides for determining the 3D coordinates of an object. This can be accomplished in that the 3D coordinates are calculated by correlating identical features in a plurality of, at least two, 2D images. By means of this method, associated identical image points can be found in two or more 2D images, which were recorded from different directions. By means of the calibration of the cameras and a triangulation or bundle triangulation, the 3D coordinates of the object points thus can be calculated. To be able to clearly make an allocation of the same features in the 2D images, patterns are projected. In this method, the projectors are not part of the calibration; they are independent of the photogrammetric camera system.

It is, however, also possible to perform other methods for determining the 3D coordinates of the object. In particular, methods of the "single-image measurement technique" can be employed, i.e. methods by which the 3D coordinates of the object can be calculated from a single 2D image. To be able to perform this method and to avoid a plurality of sequential 2D images of the same region, the recorded 2D image must contain all information for calculating the 3D coordinates. To ensure this, a pattern usually is projected onto the object. To be able to project this pattern, different properties of the light can be utilized. For instance, the pattern can be a cross grating with different colors, as it is described in DE 102 12 364 A1. In this method, the projector must be calibrated together with the camera. The method can be performed such that the 3D coordinates are calculated by using the 2D image from a camera and the projected pattern, and that these 3D coordinates are correlated and optimized by using the coordinates calculated from a 2D image from another camera and from the projected pattern.

The tracking system to be used selectively can be an optical or an interferometric tracking system. It is, however, also possible to realize the tracking system by sensors attached to the scanner for detecting the location and orientation of the scanner and/or acceleration sensors and/or gyrometers, by means of which speed and position of the scanner can be inferred by time integration. The acceleration sensors can supply three items of translation information. The gyrometers can supply three items of rotation information, i.e. information on the orientation of the scanner.

Particularly advantageously, both acceleration sensors and gyrometers are provided, to thereby obtain 6D information.

The invention claimed is:

1. A scanner for scanning one or more teeth (13, 14, 15) in a mouth of a patient, comprising:
a handle part (3); and
a carrier (2) attached to the end of the handle part, the carrier including:
a plurality of projectors (4) for projecting a pattern onto the one or more teeth, each projector including:
a light source (6);
a mask (7); and
a projector optics (8), and
a plurality of cameras (5) for recording the one or more teeth are provided in an array, each camera including:
an image sensor (9); and
a camera optics (10),
wherein all of the projector optics (8) and all of the camera optics (10) are combined to and positioned on one system optics (11), the system optics (11) being formed of one piece; and
wherein the projector optics (8) do not overlap with each other on the system optics (11), and the camera optics (10) do not overlap with each other on the system optics (11).

2. The scanner according to claim 1, wherein the projectors (4) and cameras (5) are provided on the carrier (2) in a two-dimensional arrangement.

3. The scanner according to claim 2, wherein the projectors (4) and the cameras (5) are alternately arranged on the carrier (2).

4. The scanner according to claim 3, wherein the projectors (4) each comprise a light source (6), a mask (7) and a projector optics (8).

5. The scanner according to claim 4, wherein the mask (7) and the projector optics (8) form a composite unit.

6. The scanner according to claim 2, wherein the mask (7) and the projector optics (8) form a composite unit.

7. The scanner according to claim 1, wherein the projectors (4) and the cameras (5) are alternately arranged on the carrier (2).

8. The scanner according to claim 7, wherein the mask (7) and the projector optics (8) form a composite unit.

9. The scanner according to claim 7, wherein the projectors each comprise a pattern projector and a projector optics.

10. The scanner according to claim 1, wherein the mask (7) and the projector optics (8) form a composite unit.

11. The scanner according to claim 1, wherein the projectors each comprise a pattern projector and a projector optics.

12. The scanner according to claim 1, wherein the carrier (2') has angled regions (18).

13. The scanner according to claim 1, wherein the carrier (2, 2') has the shape of a dental arc.

14. A device for determining the 3D coordinates of one or more teeth (13, 14, 15) in a mouth of a patient, comprising:
a scanner (1) for scanning an object, the scanner including:
a handle part (3); and
a carrier (2) attached to the end of the handle part, the carrier including:
a plurality of projectors (4) for projecting a pattern onto the one or more teeth, each projector including:
a light source (6);
a mask (7); and
a projector optics (8), and
a plurality of cameras (5) for recording the one or more teeth are provided in an array, each camera including:
an image sensor (9); and
a camera optics (10); and
a computer to determine the 3D coordinates of the object from the images recorded by the scanner,
wherein all of the projector optics (8) and all of the camera optics (10) are combined to and positioned on one system optics (11), the system optics (11) being formed of one piece; and
wherein the projector optics (8) do not overlap with each other on the system optics (11), and the camera optics (10) do not overlap with each other on the system optics (11).

15. The device according to claim 14, comprising a tracking system for determining the location and orientation of the scanner (1).

* * * * *